(12) United States Patent
Gibson et al.

(10) Patent No.: US 9,463,074 B2
(45) Date of Patent: Oct. 11, 2016

(54) DEVICES, SYSTEMS, AND METHODS FOR NON-INVASIVE IMAGING OF ANATOMY

(75) Inventors: Luke Andrew Gibson, Southaven, MS (US); Mark Joseph Buisseret, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 714 days.

(21) Appl. No.: 13/813,040

(22) PCT Filed: Aug. 4, 2011
(Under 37 CFR 1.47)

(86) PCT No.: PCT/US2011/046647
§ 371 (c)(1),
(2), (4) Date: Sep. 25, 2013

(87) PCT Pub. No.: WO2012/019045
PCT Pub. Date: Feb. 9, 2012

(65) Prior Publication Data
US 2014/0123781 A1    May 8, 2014

Related U.S. Application Data (60) Provisional application No. 61/370,747, filed on Aug. 4, 2010.

(51) Int. Cl.
*A61B 90/00* (2016.01)
*A61B 19/00* (2006.01)
*A61B 17/00* (2006.01)

(52) U.S. Cl.
CPC ............... *A61B 19/54* (2013.01); *A61B 90/39* (2016.02); *A61B 2017/00694* (2013.01); *A61B 2090/3954* (2016.02); *A61B 2090/3966* (2016.02)

(58) Field of Classification Search
None
See application file for complete search history.

(56) References Cited

U.S. PATENT DOCUMENTS

| 2,146,972 | A | * | 2/1939 | Miller | 84/477 B |
| 2,450,545 | A | * | 10/1948 | Foster | 84/477 B |
| 3,636,811 | A | * | 1/1972 | Bailey | 84/477 B |
| 3,810,411 | A | * | 5/1974 | Schambacher | 84/477 B |
| 4,881,736 | A | * | 11/1989 | Fox | A63B 59/00 473/417 |
| 5,639,245 | A | * | 6/1997 | McMains | G09B 19/00 206/457 |
| 5,827,108 | A | * | 10/1998 | Spector | 446/266 |
| 7,780,681 | B2 | * | 8/2010 | Sarin et al. | 606/130 |
| 2009/0149862 | A1 | * | 6/2009 | Kim | 606/104 |

FOREIGN PATENT DOCUMENTS

| WO | 9835720 | A2 | 8/1988 |
| WO | 2007017771 | A2 | 2/2007 |
| WO | 2007081679 | A2 | 7/2007 |

OTHER PUBLICATIONS

International Search Report, International Application No. PCT/US2011/046647, Date of Mailing Apr. 20, 2012, 3 pages.

* cited by examiner

*Primary Examiner* — Robert R Raevis
(74) *Attorney, Agent, or Firm* — Taft Stettinius & Hollister LLP

(57) ABSTRACT

The devices, systems, and methods described herein facilitate determining whether a patient moved during an imaging procedure causing potentially significant inaccuracies. In some, embodiments, the devices, systems and methods may also or alternatively facilitate correcting the information obtained from the MRI or other imaging procedure in view of the patient's movement or other inaccuracy creating event. There is provide a reference device (100,700,800, 900) including a rod (110,710,810,1010) having a known length, a first end (112), and a second end (224); and one or more opaque markers (120,130) connected to each of the ends.

17 Claims, 9 Drawing Sheets

DEVICES, SYSTEMS, AND METHODS FOR NON-INVASIVE IMAGING OF ANATOMY

CROSS-REFERENCE TO RELATED APPLICATIONS

This application is a United States National Phase filing of International Application No. PCT/US11/046647 filed on Aug. 4, 2011 which claims the benefit of U.S. Provisional Patent Application No. 61/370,747, filed Aug. 4, 2010. The disclosure of both of these prior applications are incorporated by reference in their entirety.

BACKGROUND OF THE INVENTION

1. Field of the Invention

The present invention relates generally to surgery and more specifically to image analysis through computer assisted medical diagnostics.

2. Related Art

Magnetic Resonance Imaging (MRI) is a non-invasive medical imaging technology that uses electromagnetic fields to create one or more high contrast cross-sectional images or slices of the internal anatomy. Using automated, semi-automated or manual processing techniques, the images can be stacked, segmented and otherwise processed to create computer assisted design (CAD) models or other types of three-dimensional models of the anatomy of interest. For instance, MRI images can be processed to create a three dimensional model of the surface contours and geometries of the bone and/or cartilage of a patient's joint. Other types of non-invasive imaging techniques can be used to create three dimensional models of bones, joints and other anatomy as well, including, without limitation, Computed Tomography (CT) imaging or ultrasound imaging.

It is known to use three-dimensional models in some instances to create orthopaedic implants and/or instrumentation that is adapted to specifically correspond to the anatomy of a particular patient. For instance, it is known to use three-dimensional models of a femur and/or tibia to build one or more cutting guides with an anatomy-contacting surface that is specifically designed to reference and correspond to the anatomy of a particular patient and to guide a cutter to form one or more resections on the bone in desired positions and orientations relative to that anatomy and certain important axes of that anatomy. Three-dimensional models and other information obtained from these non-invasive imaging techniques can be used in other contexts as well outside of the development of patient specific instruments and implants.

In some instances, it may be important for the patient to remain as motionless as possible during imaging, as movement can create inaccuracies in the process that could potentially negatively impact on the later use of the information obtained from the imaging to treat the patient. For instance, when an MRI procedure is used to obtain information to create a patient specific instrument for facilitating a knee arthroplasty procedure, it is, at least in some procedures, necessary to scan several portions of the patient's anatomy, such as, in some cases, the ankle, knee and hip. In some instances, it may be important to maintain the spatial relationship between the ankle, knee and hip scans to determine an appropriate position and orientation of the patient specific instrument or other orthopaedic device. For instance, in some instances, those relationships may be used to determine a mechanical axis, anatomic axis, or other important axis of the knee joint, or other references associated with this or other portions of the anatomy, which may be, in some cases, important references and information for properly aligning a cutting guide or other instrument or implant with respect to the bone. For instance, knowing the mechanical axis of the knee joint may be important for establishing the varus/valgus alignment of the cutting guide or other degrees of freedom associated with the positioning and orienting of the cutting guide in three dimensional space. If the patient moves during one of the scans, or in between one of the scans, it may change the relationship between the anatomy associated with the ankle, knee and/or hip with respect to the data obtained through the imaging procedure, and could potentially negatively impact on the quality of the data obtained, and consequently the quality of the patient specific instrument or implant created using that data.

In some procedures, an additional x-ray of the entire leg or other anatomy of interest may be performed as a check against the possibility that the relationship between the relevant anatomy changed during the imaging procedure. The additional x-ray adds expense to the pre-surgical planning, and there remains a need in the art for a way to verify the relationship between the relevant anatomy did not change during the imaging procedure at a lower cost.

SUMMARY OF THE INVENTION

Described herein are examples of devices, systems and methods for imaging anatomy, such as by, but not limited to, MRI, CT or ultrasound procedures, devices, systems and methods, that address some or all of the above concerns and/or other drawbacks or problems associated with imaging procedures. In some instances, the devices, systems and methods described herein may facilitate determining whether a patient moved during an MRI or other imaging procedure causing potentially significant inaccuracies, or whether other events occurred that caused potentially inaccurate data. In some, but not necessarily all, embodiments, the devices, systems and methods described herein may also or alternatively facilitate correcting the information obtained from the MRI or other imaging procedure in view of the patient's movement or other inaccuracy creating event. Although the devices, systems and methods described herein are discussed in the context of an MRI procedure, other image based procedures could also employ the teachings disclosed herein for similar or other purposes.

In one aspect, there is provided a reference device comprising: a rod having a known length, a first end, and a second end; and at least one marker connected to each of said first end and said second end. In some embodiments, at least one marker appears opaque to an imaging device. In one particular embodiment, there are at least three markers connected to each of said first end and second end, and the at least three markers are removably positioned to form a plane. In an alternative embodiment, the rod is segmented. In some embodiments, the rod further comprises a hinge. In some embodiments, there are at least four markers connected to each of said first end and second end, and the at least four markers are removably positioned to form a coordinate system.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

Figure 1:
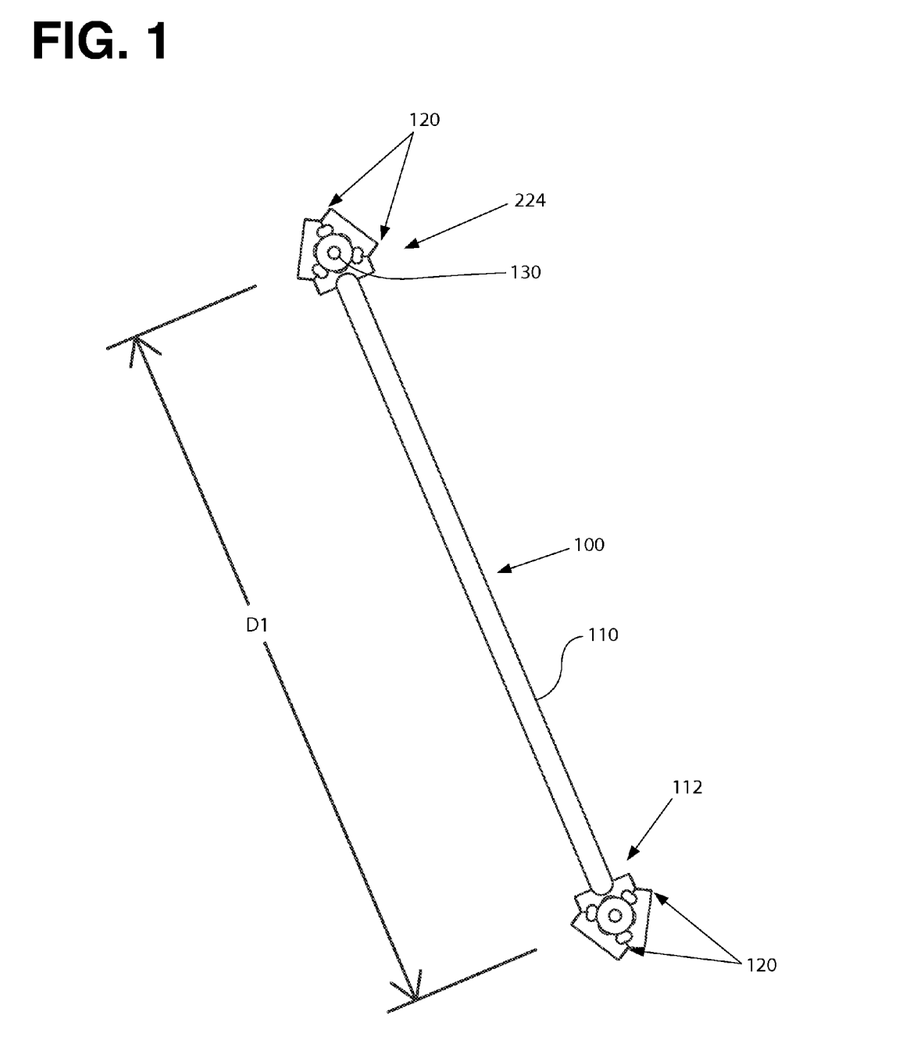
FIG. 1 illustrates a reference device in a first embodiment.

FIG. 1 shows a reference device 100. The reference device 100 includes a rod 100 with a first end 112 and a second end 224. Fiducial markers 120 are connected to each end 112,224. In some embodiments, the markers 120 may be opaque to the particular imaging technology employed. For instance, in some embodiments, the markers 120 may appear opaque or semi-opaque in an MRI image ("MRI opaque") or may appear opaque or semi-opaque in a X-Ray image ("radio opaque"). In other embodiments, the markers 120 are not opaque or semi-opaque to the particular imaging technology used, but are otherwise capable of indicating a reference point or points on an MRI or other image. In some embodiments, separate markers are not necessary and portions or components of the reference device 100 itself function as virtual or actual markers. As an example, the fiducial markers may be linear fiducial markers having a capsule filled with pure water, vitamin E, or fish oil. Alternatively, the fiducial marker may be a spherical bead. Those having ordinary skill in the art would understand that other types of fiducial markers may be used. In some embodiments, the marker may be identified a bright spot or bright line on the MRI image, and the bright spot or line may also be seen on the dicom data when the image data is converted to CAD data such that marker may be located in the coordinate system of the CAD model or used to generate a coordinate system within the CAD model.

In the embodiment shown in FIG. 1, each end 112, 224 of the reference device 100 includes four markers, although, in other embodiments, the reference device 100 may include more or less markers at each end of the device. On each end 112, 224, there is a plurality of substantially tube-shaped holders and each holder receives a cylindrical pill shaped marker 120. The markers 120 are removably positioned to define a plane as schematically illustrated by the triangles shown in FIG. 1. Additionally, a spherical shaped bead marker 130 is positioned at the center of the triangle or at the end of the rod of the reference device.

Figure 6:
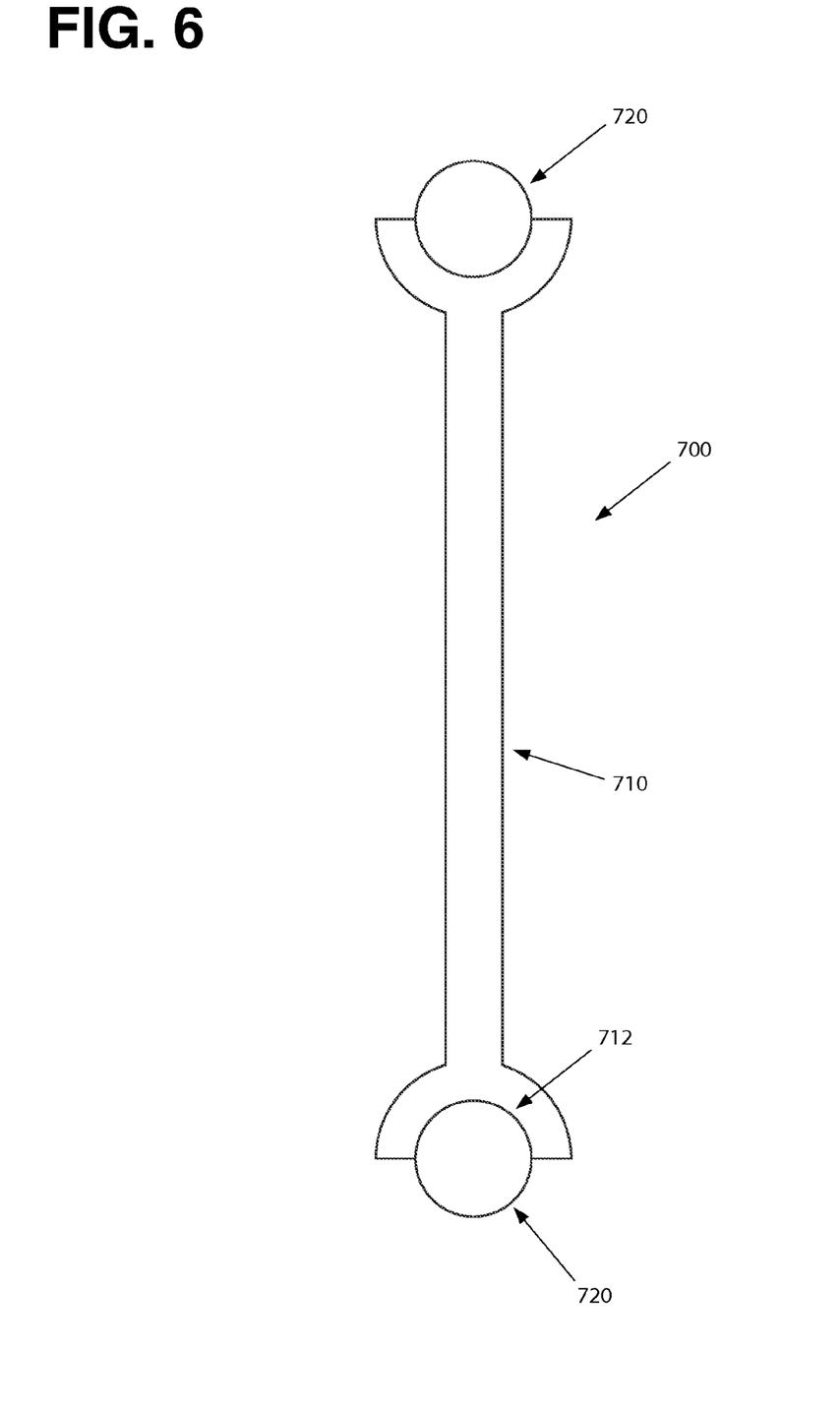
FIG. 6 illustrates the reference device in a third embodiment.
Figure 7:
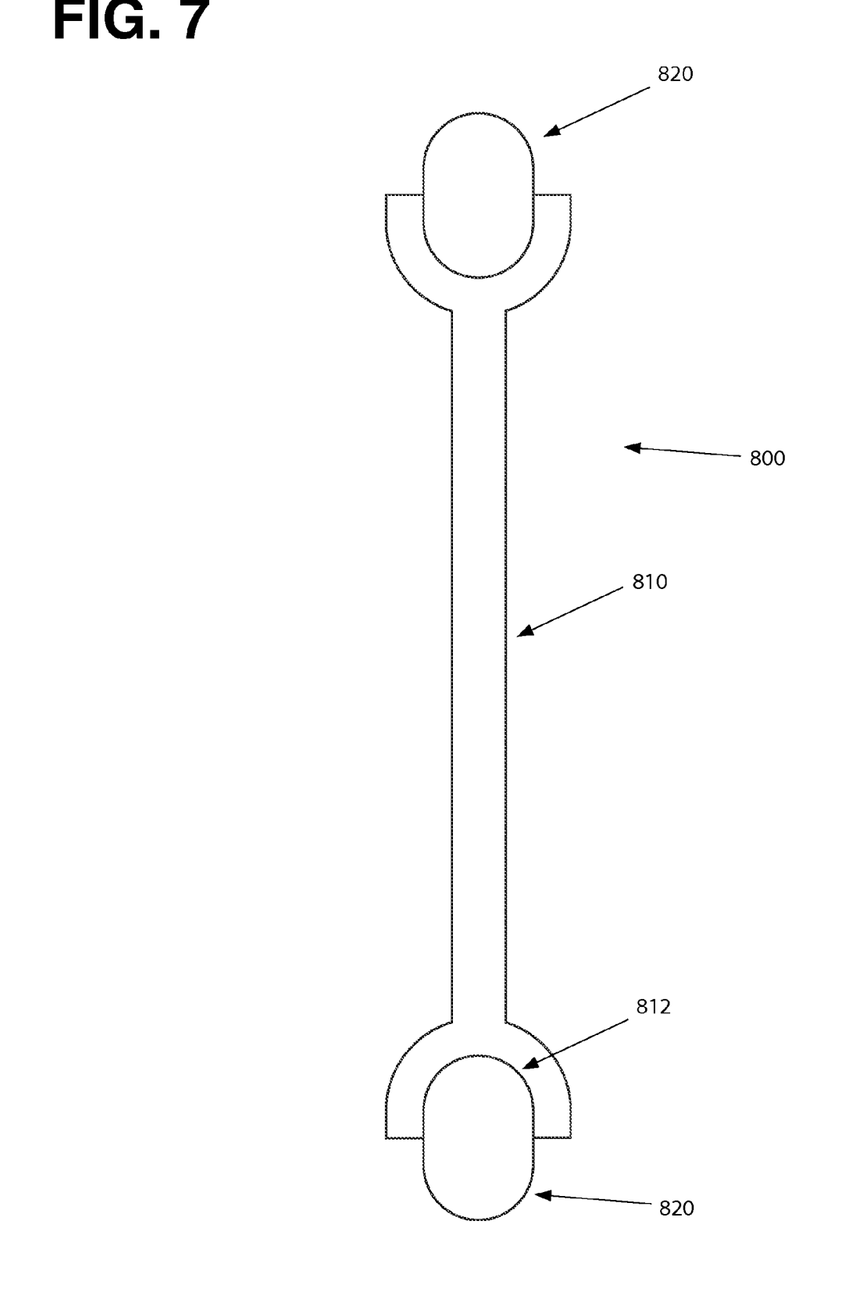
FIG. 7 illustrates the reference device in a fourth embodiment.

In other embodiments, each end of the reference device may include only one marker. FIGS. 6 and 7 illustrate additional alternative embodiments of reference devices 700, 800. FIG. 6 shows a reference device 700 having a rod 710 with a cup shaped depression 712 at each end for receiving a single spherical bead-shaped marker 720. FIG. 7 shows a reference device 800 having a rod 810 with a cup shaped depression 812 at each end for receiving a single pill or cylindrical shaped marker 820. In these or other embodiments, the rod 810 may be a non-ferrous material such as wood, plastic, some types of metals, or another non-ferrous material.

In some embodiments, the markers may have any desired shape and/or silhouette. In some embodiments, the markers may each have a distinctive shape and/or silhouette to facilitate distinguishing one marker from another. In some embodiments, the markers are containers that hold an MRI opaque or semi-opaque liquid or a liquid that is opaque or semi-opaque to other types of imaging techniques.

In the embodiment shown in FIG. 1, the reference device 100 at least temporarily holds the marker(s) 120,130 on one end 112 in fixed positions and/or orientations with respect to the marker(s) 120,130 on the other end 224 of the device. Accordingly, in at least some embodiments, the marker(s) on one end of the device are at a fixed/known distance from the marker(s) on the other end of the device. In some embodiments, a length of the rod 110 or other aspects of the reference device may be adjusted, modified, or otherwise changed to alter the distance between the markers 120 to another known distance, for instance, to allow the device to be used with different patients of various heights. Thus, the reference device may be provided in sets of different known lengths or the reference device may be adjustable to various pre-determined lengths. As an example, the reference device may be provided in a set of 2 foot, 3 foot, 4 foot, and 5 foot devices. In some embodiments, the reference device 100 may be relatively straight, but in other embodiments, the reference device 100 may be bowed slightly or substantially to conform to different portions of the anatomy.

Figure 8:
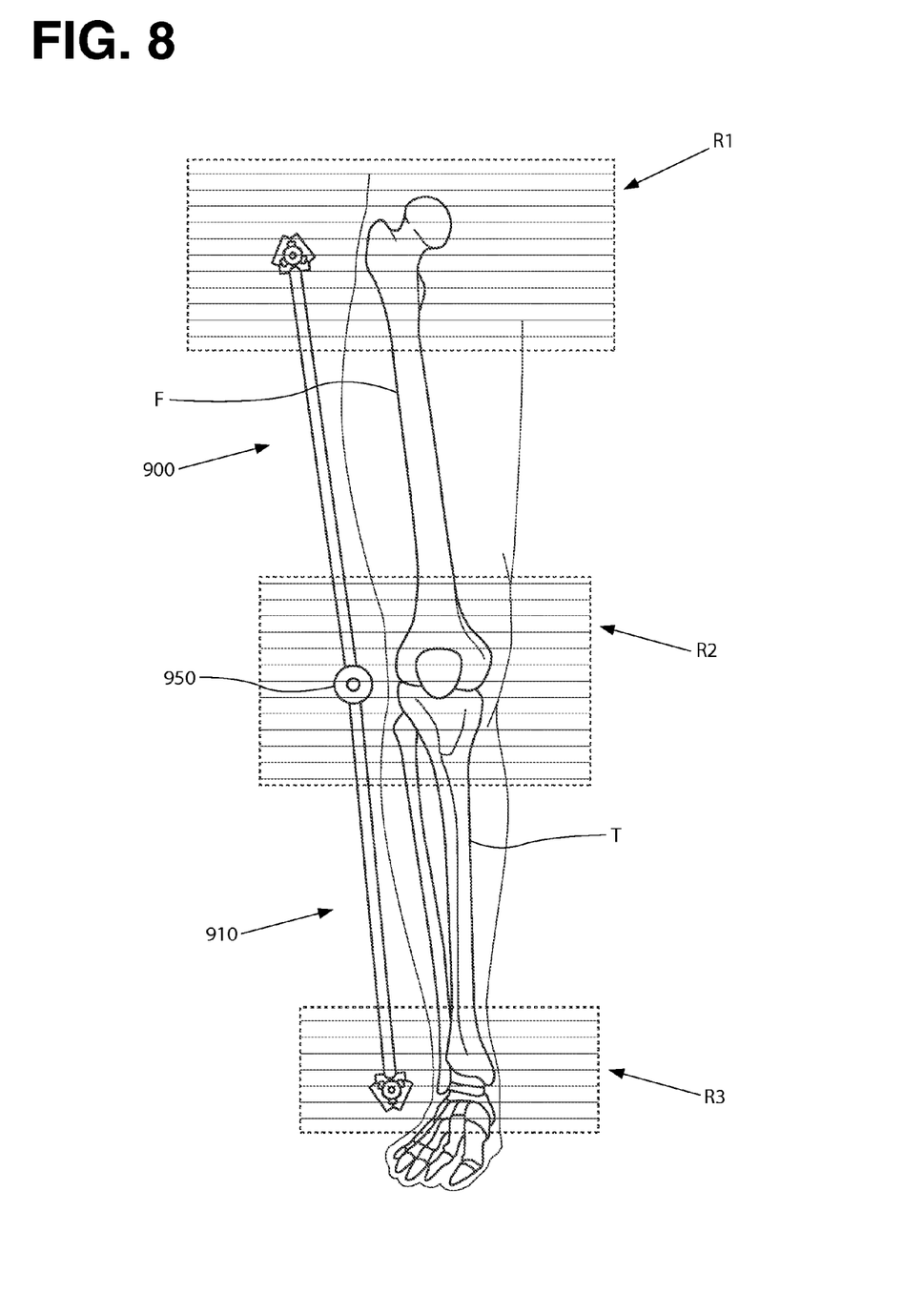
FIG. 8 illustrates the reference device in a fifth embodiment.

In some embodiments, the reference device may be hinged as shown in FIG. 8. The reference device 900 has a hinge 950. The hinge 950 allows the device 900 to more closely follow the contours of the patient's leg. Hinged reference devices could also be used in other contexts as well, for example, the shoulder area.

In some embodiments, the reference device 100, 700, 800, 900 is adapted to be fixed or at least temporarily held in place against the patient's body. In some embodiments, the reference device may be simply taped to the patient's body. Although, in other embodiments, the reference device 100, 700, 800, 900 may be positioned in other manners and may incorporate structures or features to facilitate such positioning. In still other embodiments, the reference device 100, 700, 800, 900 does not remain on the patient's body but is only used to position markers onto the patient's body and then removed once the markers have been positioned on the patient's body. For instance, in some embodiments, the markers include a surface with a contact or other type of adhesive that secures the marker to the patient, and the reference device can be used to position two or more markers on the patient at a known distance from one another and then removed.

Figure 2:
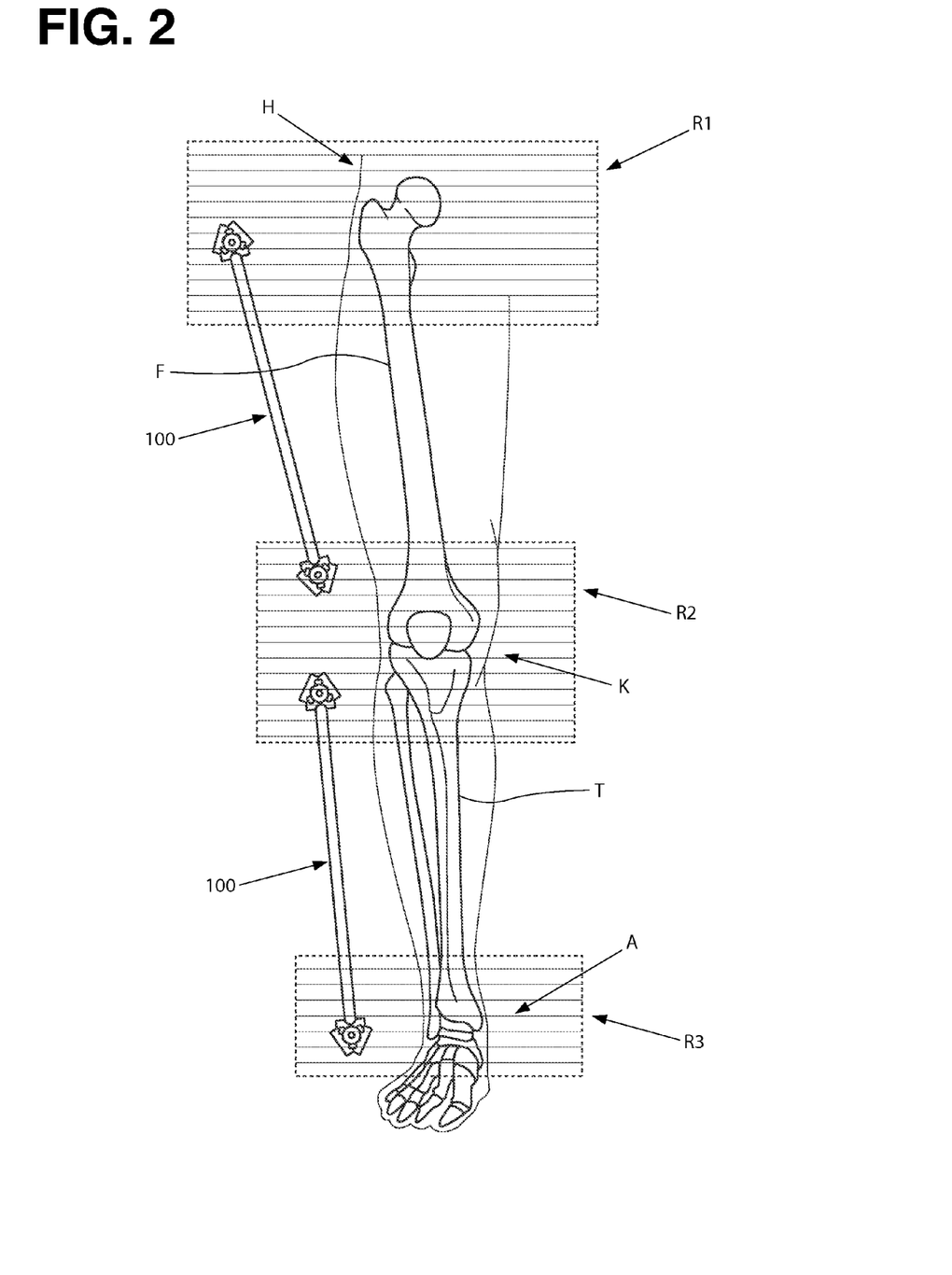
FIG. 2 illustrates two reference devices in use.

FIG. 2 schematically illustrates two of the reference devices 100, 700, 800, 900 positioned against a patient's body. As shown in FIG. 2, in some embodiments, one of the reference devices 100, 700, 800, 900 may be positioned with a first end and its associated markers proximate the patient's hip H or proximal femur F—in a first scan area R1 and the second end and its associated markers proximate the patient's knee K or distal femur F in a second scan area R2. In the embodiment of FIG. 2, the second reference device 100, 700, 800, 900 is positioned with a first end and its markers proximate the patient's knee K or proximal tibia T in the first scan area R2 and a second end and its associated marker proximate the patient's ankle A or distal tibia T in a third scan area R3.

In the embodiment of FIG. 2, the positioning of the two reference devices described in the preceding paragraph helps to preserve and identify in the imaging data the spatial relationship between the patient's hip H, knee K and ankle A. For instance, in some embodiments, the reference devices 100, 700, 800, 900 could be used to relate two or more bones with respect to one another in the imaging data. In these or other embodiments, the reference devices could be used to relate two or more joints with respect to one another in the imaging data.

FIG. 2 is illustrative of one embodiment of the devices, systems and methods disclosed herein, and other positions and orientations of two or other numbers of reference devices having two or additional markers or sets of markers each are possible. FIG. 2 illustrates an embodiment using two reference devices positioned for obtaining image data to be used in conjunction with a knee arthroplasty, and other arrangements and types of reference devices are envisioned for other types of procedures, including, but not limited to, hip and shoulder procedures. Nor does FIG. 2 illustrate the only possible configuration of reference devices and associated markers for a knee arthroplasty. In some knee arthroplasty related procedures, it may not be necessary to image the same regions illustrated in FIG. 2, and, for instance, may only be necessary to image some or all of the patient's knee joint. Moreover, in some embodiments, a single reference device may be used instead of two separate devices. In some embodiments, the single reference device could include a hinge or an angular component.

For instance, in the embodiment illustrated in FIG. 2, it may be possible to substitute a single reference device spanning the femur and tibia instead of the two separate devices. In some embodiments, however, it may be desirable to have a separate reference device for each bone or bone portion.

In the embodiment shown in FIG. 2, the reference devices are positioned on the patient's body before the imaging procedure and remains in place during at least a portion of the procedure. In some embodiments, such as some examples of MRI procedures done in preparation for a knee arthroplasty, a first scan is performed of the patient's anatomy proximate the ankle. Next, the table on which the patient lies translates along one or more axes or otherwise moves to move the next portion of the patient's anatomy into position for a second scan, in this particular embodiment, of the patient's anatomy proximate the knee joint. In some embodiments, the computer system or other functionality that is part of or is associated with the MRI device records or otherwise track or indicate the distance and/or direction that the table has been moved between the first and second scans. Next, the table translates or otherwise moves to the next portion of the patient's anatomy into position for a third scan, in this particular embodiment, of the patient's anatomy proximate the patient's hip.

Figure 3:
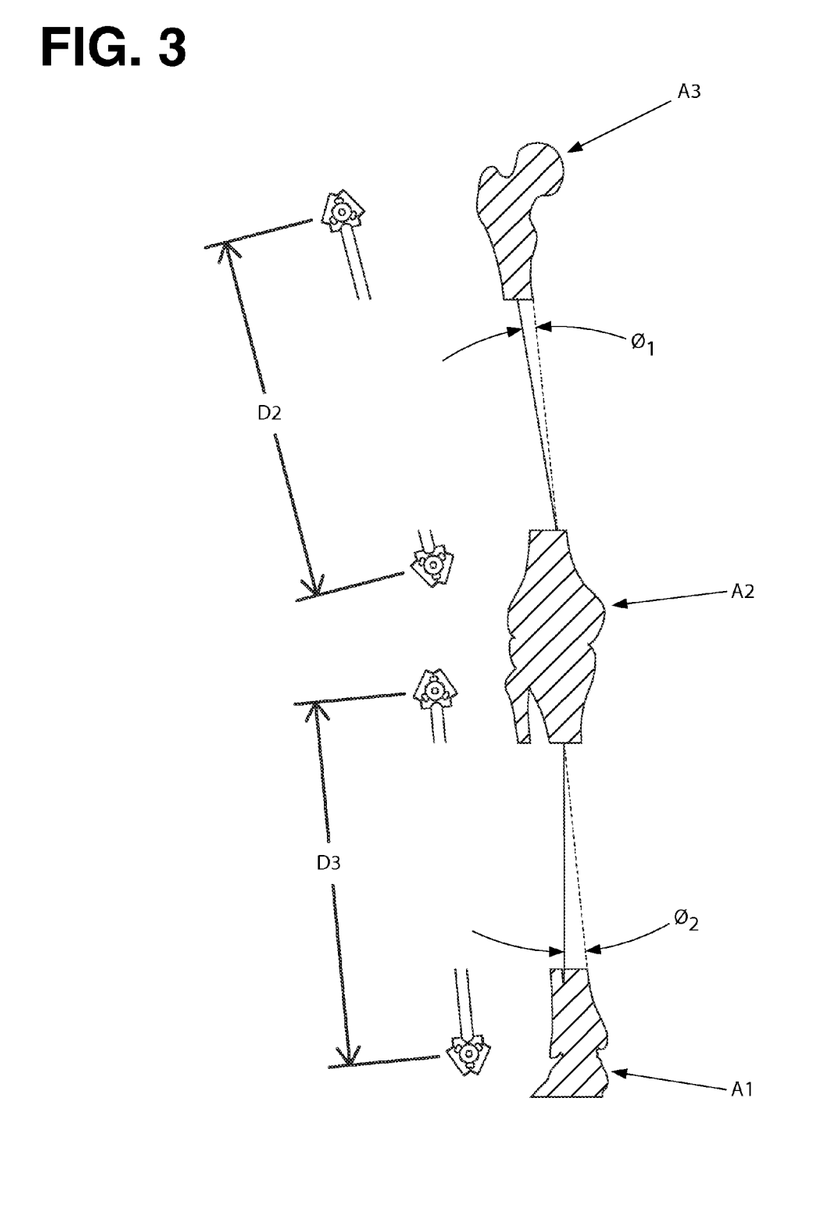
FIG. 3 is a schematic illustrating a method of use of the first embodiment.

FIG. 3 schematically illustrates some of the information obtained from the first, second and third MRI scans described above for the embodiment of FIG. 2. In the embodiment of FIG. 3, information about: (1) the known distance and orientation between the markers or sets of markers of the reference device(s); (2) the known translation distance or other movement of the MRI table between scans; and (3) the distance and orientation between the markers or sets of markers as measured or otherwise determined from the image data, may, in some embodiments, be used to determine the accuracy and/or quality of the data obtained through the imaging procedure. For instance, without limitation, if the measured distance between the markers of one of the reference devices deviates from the actual distance of the markers on the reference device, that may indicate that the patient shifted or otherwise moved on the MRI table during the imaging procedure or that another event occurred that could negatively impact on the quality or accuracy of the imaging data obtained.

For instance, in some embodiments, the distances between the markers in the MRI images can be measured (either manually or using automated or semi-automated technologies) and compared to the known distances between the actual markers on the actual reference device(s). If the measured distance is not the same or substantially the same as the actual distance, that may indicate to the MRI operator or other individual examining the image data that the patient moved at some point during the MRI procedure. In some embodiments, these distances or other aspects of the MRI or other data may be checked immediately after or during the MRI procedure (using automated, semi-automated, or manual techniques) to indicate whether the MRI procedure needs to be re-started or re-performed. In other embodiments, these distances or other aspects of the MRI or other data can be examined later after the completion of the MRI procedure. The ability to verify the accuracy of the MRI image is significant as it may allow for the omission of an additional x-ray, thereby reducing overall costs to the pre-surgical plan.

In some embodiments, the devices, systems and methods described herein can be used to not only indicate whether there may be some inaccuracy in the imaging data, but also whether and how to correct such inaccuracy. For instance, in some embodiments, the devices, systems and methods described herein can facilitate determining how to modify or manipulate the data obtained through the imaging procedure such that the data reflects the actual relationship between the patient's anatomy, such as, in some embodiments, the proper relationship between the bones and/or joints associated with the patient's hip, knee and ankle.

For instance, in some embodiments, the deviation between the known distances and other relationships of the markers or sets of markers and the distances and other relationships of the markers or sets of markers shown in the imaging data can be used to determine the types and extent of any transitional and/or rotational movements that occurred during or between the scans. This information, in some embodiments, may be sufficient to determine how to correct the imaging data to account for the movement such that the three sets of image data (corresponding to the three scans described in the particular embodiment above), or later information files corresponding to the three sets of image data, can be modified to offset or otherwise account for the movement that occurred. In other embodiments, however, these additional steps are unnecessary and the information obtained from the devices, systems and methods described herein can be used in other ways.

Figure 4:
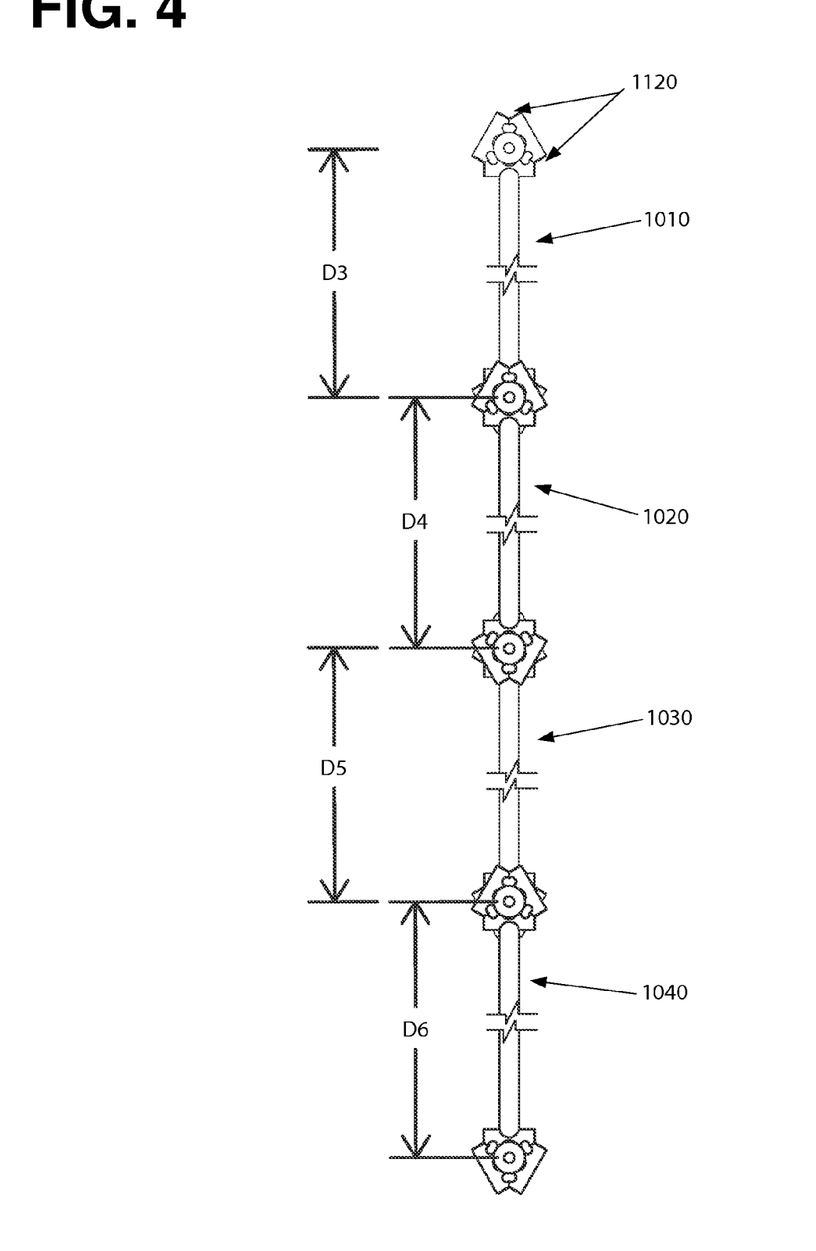
FIG. 4 illustrates the reference device in an alternative embodiment

FIG. 4 illustrates an alternative embodiment of a reference device. In the embodiment of FIG. 4 the rod is segmented such that the overall length of the device (and consequently the length between certain markers associated with the device) can be changed. For instance, in some embodiments, it may be desirable to adjust the reference device to accommodate patients have a range of heights or other attributes. In some embodiments, each segment could be unique and/or could be identified uniquely, and each segment could be designed to have specific connecting elements such that it only attaches to another unique segment in a unique order (e.g. segment 1 can only attach to one end of segment 2, etc.). In this manner, in some embodiments, it will be relatively easy to determine the relationship between the markers associated with the segments. Some embodiments could include a set of reference devices having different lengths, with particular lengths of reference devices intended for use with patient's having particular heights or other attributes.

Figure 5:
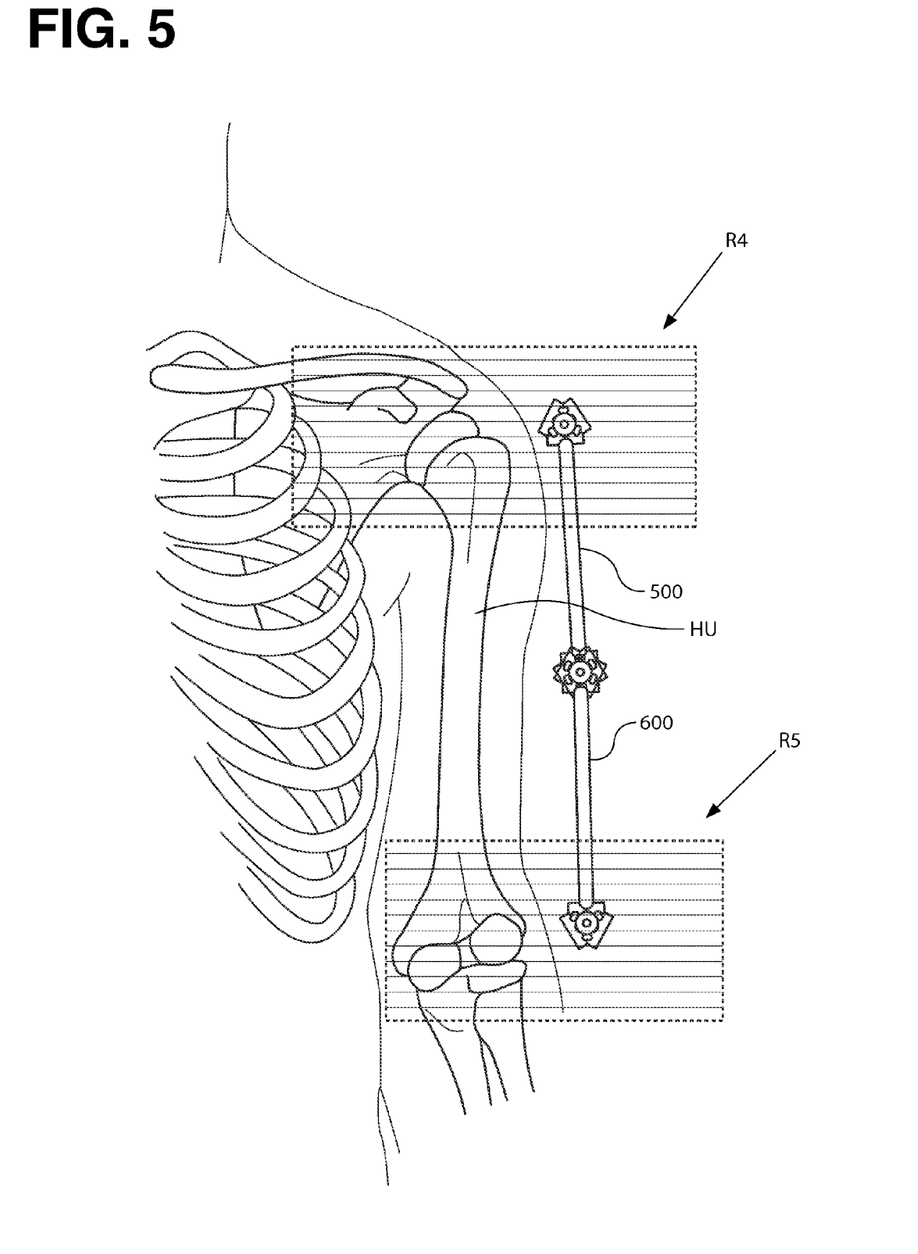
FIG. 5 is a schematic illustrating a method of use of the second embodiment.

FIG. 5 illustrates one possible use of the segmented reference device of FIG. 4. Alternatively, a pair of reference devices could be positioned with respect to a patient's elbow, with one reference device positioned to extend generally along the patient's radius and ulna and another reference device positioned to extend generally along the patient's humerus. In other embodiments, these or similar reference devices, systems and methods could be used in imaging procedures involving the ankle or shoulder joints. In still other embodiments, these or similar referencing devices, systems and methods could be used in imaging procedures relating to trauma matters, such as traumatic injuries involving complicated fractures with several bone segments of one or more bones that require complicated translations and rotations for correction.

Figure 9:
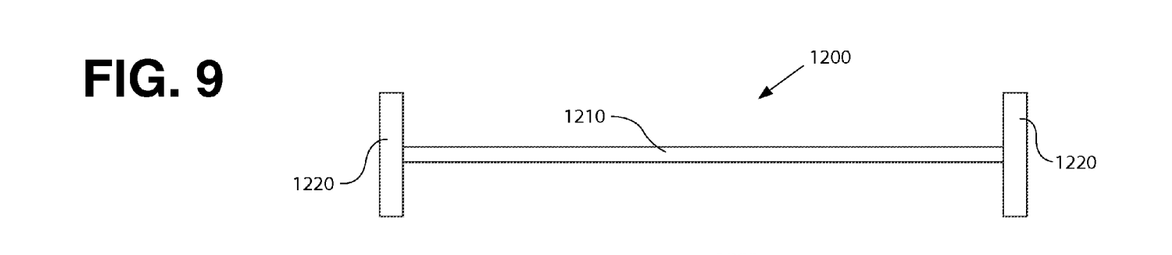
FIG. 9 illustrates a side view of the reference device.
Figure 10:
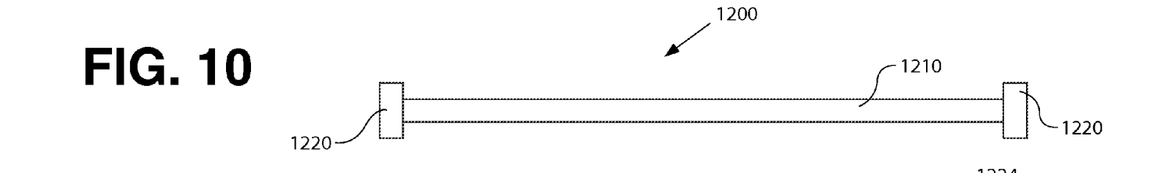
FIG. 10 illustrates a top view of the reference device.
Figure 11:
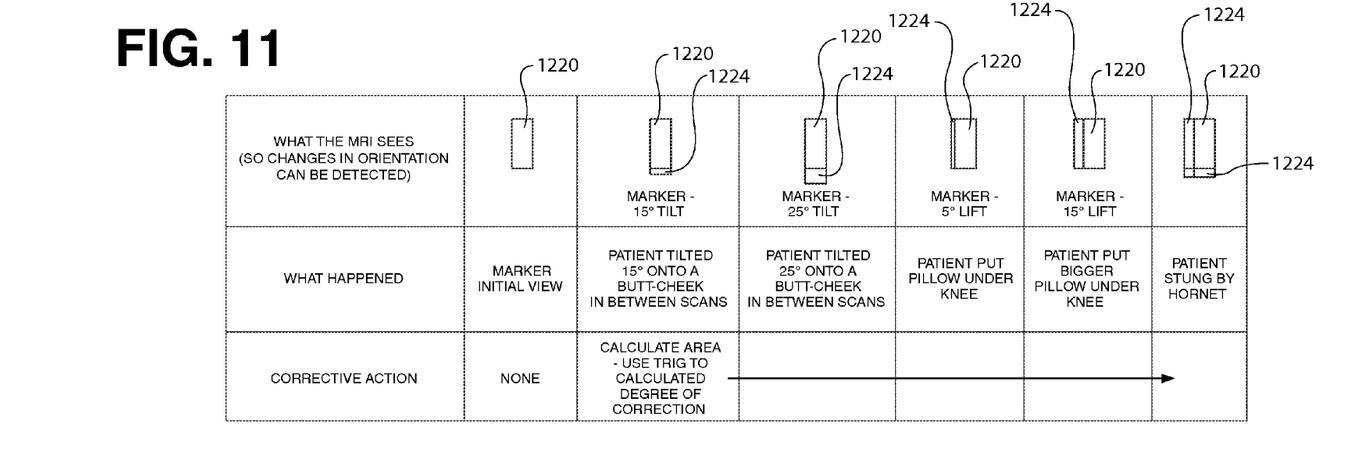
FIG. 11 schematically illustrates image corrective action based upon determined error.

FIGS. 9-11 illustrate one embodiment for a system and method for correcting image data based upon detected marker orientation. FIG. 9 illustrates a side view of the reference device 1200, and FIG. 10 illustrates a top view of the reference device 1200 shown in FIG. 9. Each marker 1220 is in the form of a rectangular block. The marker 1220 may be filled with an MRI-recognizable medium, such as pure water, vitamin E, or fish oil. The markers 1220 are in the same orientation but spaced apart a known distance. The reference device 1200 is placed on or affixed to a side of the patient such that the top of the device is orthogonal to the MRI scanning beam. FIG. 11 illustrates various examples of tilt and/or lift of one of the markers after scanning. The tilt and/or lift presents one or more perspective lines 1224 on the marker 1220. Trigonometry may be used to calculate an area created by the perspective line(s) 1224 and outside edges of the marker 1220. The calculated area may be used to adjust the orientation of the marker 1220 and the associated anatomy in the CAD model. Alternatively, the reference device 1200 is placed on or affixed to a side of the patient such that the top of the device is not orthogonal to the MRI scanning beam, a first area is calculated upon an initial scan, a second area is calculated upon a later scan, and the difference between the first and second areas can be used to determine the appropriate amount of correction for the marker and the associated anatomy in the CAD model.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A reference device comprising:
   a. a rod having a known length, a first end, and a second end; and
   b. at least three markers connected to each of the first end and the second end, and the at least three markers are removably positioned to form a plane.

2. The reference device of claim 1, wherein the at least three markers appear opaque or semi-opaque to an imaging device.

3. The reference device of claim 1, wherein the rod is segmented.

4. The reference device of claim 1, wherein the rod further comprises a hinge structured to adjust an angular position of the at least three markers at the first end relative to an angular position of the at least three markers at the second end.

5. The reference device of claim 1, further including a plurality of tubes at each of the first and second ends, the plurality of tubes arranged to receive placement of at least some of the at least three markers.

6. The reference device of claim 1, wherein at least one of the at least three markers includes a liquid that appears opaque or semi-opaque to an imaging device.

7. The reference device of claim 6, wherein the liquid comprises at least one of water, fish oil or vitamin E.

8. The reference device of claim 1, wherein the at least three makers include an adhesive structured to secure the at least three markers to a patient.

9. The reference device of claim 1, wherein the at least three markers appear opaque or semi-opaque to an imaging device.

10. A reference device comprising:
    a. a rod extending between a first end and a second end; and
    b. at least one marker connected to each of the first end and the second end, at least one of the at least one marker including a liquid and being positionable to form a coordinate system relative to at least a portion of a patient's body; and
    wherein the rod further comprises a hinge structured to adjust an angular position of the at least one marker at the first end relative to an angular position of the at least one marker at said second end.

11. The reference device of claim 10, wherein the at least one marker is removably coupled to the reference device.

12. The reference device of claim 10, wherein the first and second ends each include a curved depression sized to receive placement of at least one of the at least one marker.

13. A reference device comprising:
    a. a rod having a known length, a first end, and a second end; and
    b. at least four markers connected to each of the first end and the second end, and the at least four markers are removably positioned to form a coordinate system.

14. The reference device of claim 13, wherein at least one of the at least four markers includes a liquid that appears opaque or semi-opaque to an imaging device.

15. The reference device of claim 14, wherein the liquid comprises at least one of water, fish oil or vitamin E.

16. The reference device of claim 13, wherein at least three of the at least four markers have a similar shape that is different than a shape of at least one other of the at least four markers.

17. The reference device of claim 13, wherein the at least four makers include an adhesive structured to secure the at least four markers to a patient.

* * * * *